United States Patent [19]
Beckwith

[11] Patent Number: 5,285,777
[45] Date of Patent: Feb. 15, 1994

[54] TRACHEOSTOMY APPARATUS

[76] Inventor: Wayne E. Beckwith, P.O. Box 774 Lakeview St., Greenville, Me. 04441

[21] Appl. No.: 742,373

[22] Filed: Aug. 8, 1991

[51] Int. Cl.⁵ .................. A61M 16/00; A61M 5/32; A62B 9/06
[52] U.S. Cl. .................. 128/207.15; 128/207.17; 604/180
[58] Field of Search .......... 128/207.14, 207.15, 128/207.17, 200.26; 604/96, 102, 180

[56] References Cited

U.S. PATENT DOCUMENTS

| | | | |
|---|---|---|---|
| 3,039,469 | 6/1962 | Fountain | 128/200.26 |
| 3,225,767 | 12/1965 | Smith | 128/200.26 |
| 3,659,611 | 5/1972 | Miller | 128/207.15 |
| 3,810,474 | 5/1974 | Cross | 128/207.15 |
| 4,315,505 | 2/1982 | Crandall et al. | 128/207.15 |
| 4,405,314 | 9/1983 | Cope | 128/207.14 |
| 4,471,776 | 9/1984 | Cox | 128/207.15 |
| 4,584,998 | 4/1986 | McGrail | 128/207.15 |
| 4,637,389 | 1/1987 | Heyden | 128/207.15 |
| 4,677,978 | 7/1987 | Melker | 128/207.14 |
| 5,056,515 | 10/1991 | Abel | 128/200.26 |
| 5,067,496 | 11/1991 | Eisele | 128/207.14 |

Primary Examiner—Edgar S. Burr
Assistant Examiner—Kimberly L. Asher
Attorney, Agent, or Firm—Leon Gilden

[57] ABSTRACT

A flexible support plate member mounts straps at opposed ends thereof for securement about an individual, with the plate member receiving a tracheal tube through a receiving plate bore in pivotal relationship, with the tracheal tube including an expandable balloon seal positioned adjacent a lower terminal end of the tracheal tube, with a suction conduit arranged for reception of a catheter tube. A modification of the invention includes sealing ribs and adhesive mounted about the balloon to enhance sealing within the individual.

1 Claim, 3 Drawing Sheets

TRACHEOSTOMY APPARATUS

BACKGROUND OF THE INVENTION

1. Field of the Invention

The field of invention relates to tracheal apparatus, and more particularly pertains to a new and improved tracheostomy apparatus wherein the same is arranged for positioning within an individual during a tracheostomy procedure.

2. Description of the Prior Art

Tracheal apparatus to insert a tube into an individual's windpipe for permitting an individual to breath due to other restrictions is arranged wherein the food consumption effects difficulty in breathing. The instant invention addresses the problem by providing a suction catheter orifice permitting medical personnel to remove any secretions or debris above the cuff within the windpipe.

As such, it may be appreciated that there continues to be a need for a new and improved tracheostomy apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of tracheostomy apparatus now present in the prior art, the present invention provides a tracheostomy apparatus wherein the same provides a tracheostomy system for permitting effective insertion, positioning, and maintenance of a tracheal tube within an individual. As such, the general purpose of the present invention, which will be described subsequently in greater detail, is to provide a new and improved tracheostomy apparatus which has all the advantages of the prior art tracheostomy apparatus and none of the disadvantages.

To attain this, the present invention provides a flexible support plate member mounting straps at opposed ends thereof for securement about an individual, with the plate member receiving a tracheal tube through a receiving plate bore in pivotal relationship, with the tracheal tube including an expandable balloon seal positioned adjacent a lower terminal end of the tracheal tube, with a suction conduit arranged for reception of a suction catheter tube. A modification of the invention includes sealing ribs and adhesive mounted about the balloon to enhance sealing within the individual.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved tracheostomy apparatus which has all the advantages of the prior art tracheostomy apparatus and none of the disadvantages.

It is another object of the present invention to provide a new and improved tracheostomy apparatus which may be easily and efficiently manufactured and marketed.

It is a further object of the present invention to provide a new and improved tracheostomy apparatus which is of a durable and reliable construction.

An even further object of the present invention is to provide a new and improved tracheostomy apparatus which is susceptible of a low cost of manufacture with regard to both materials and labor, and which accordingly is then susceptible of low prices of sale to the consuming public, thereby making such tracheostomy apparatus economically available to the buying public.

Still yet another object of the present invention is to provide a new and improved tracheostomy apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
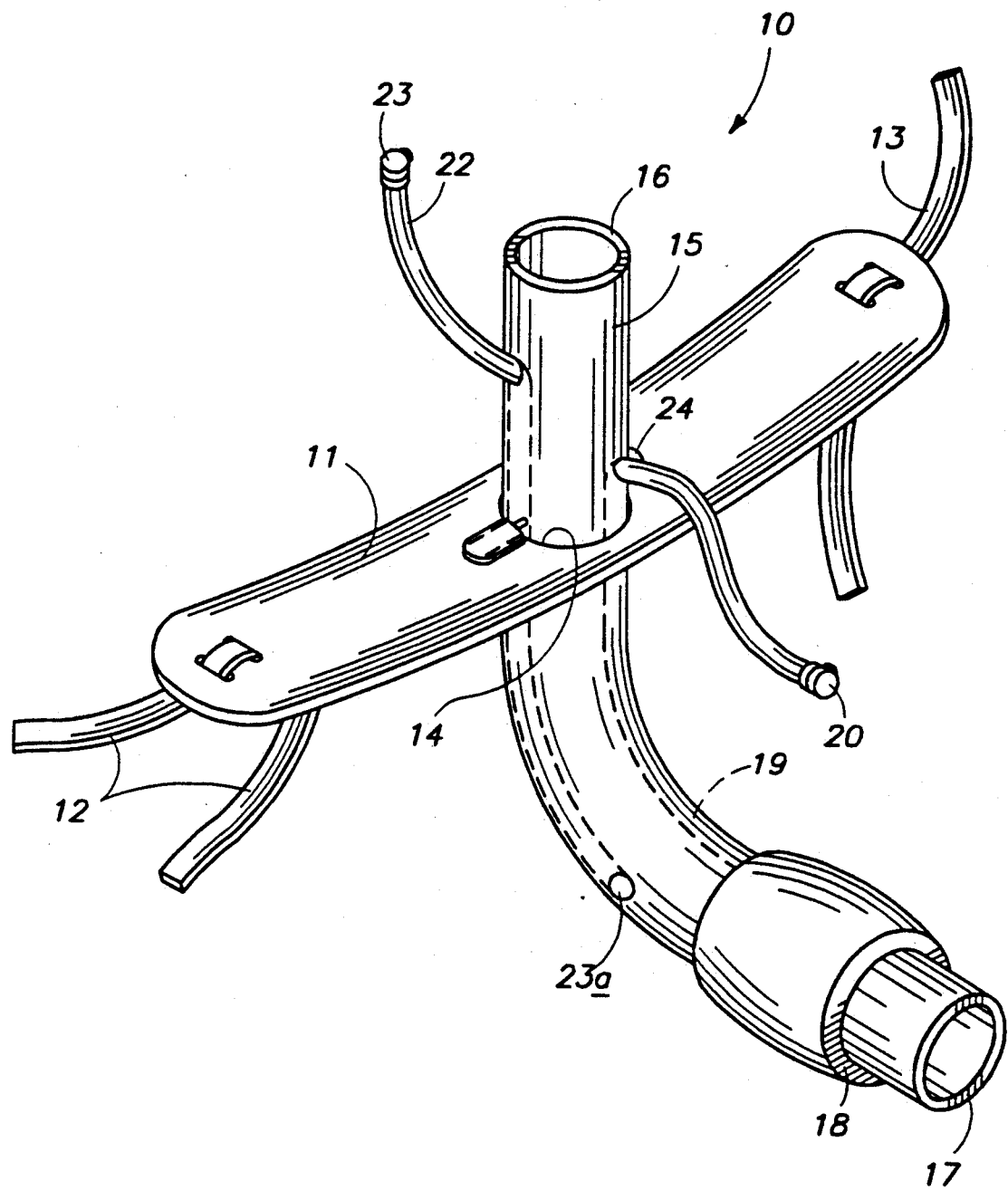
FIG. 1 is an isometric illustration of the instant invention.
Figure 2:
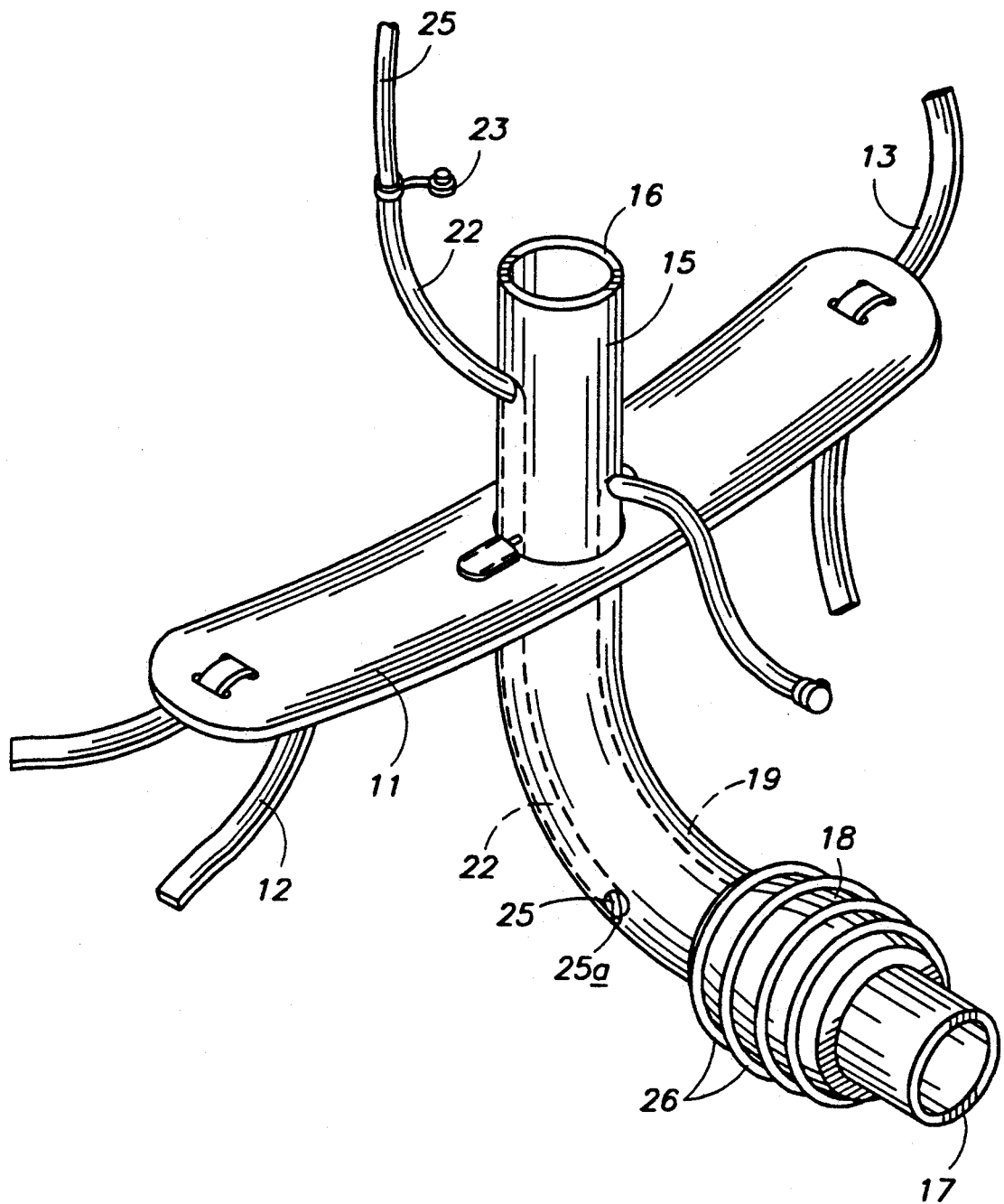
FIG. 2 is an isometric illustration of a modified expandable sealing balloon or cuff utilized by the invention.
Figure 3:
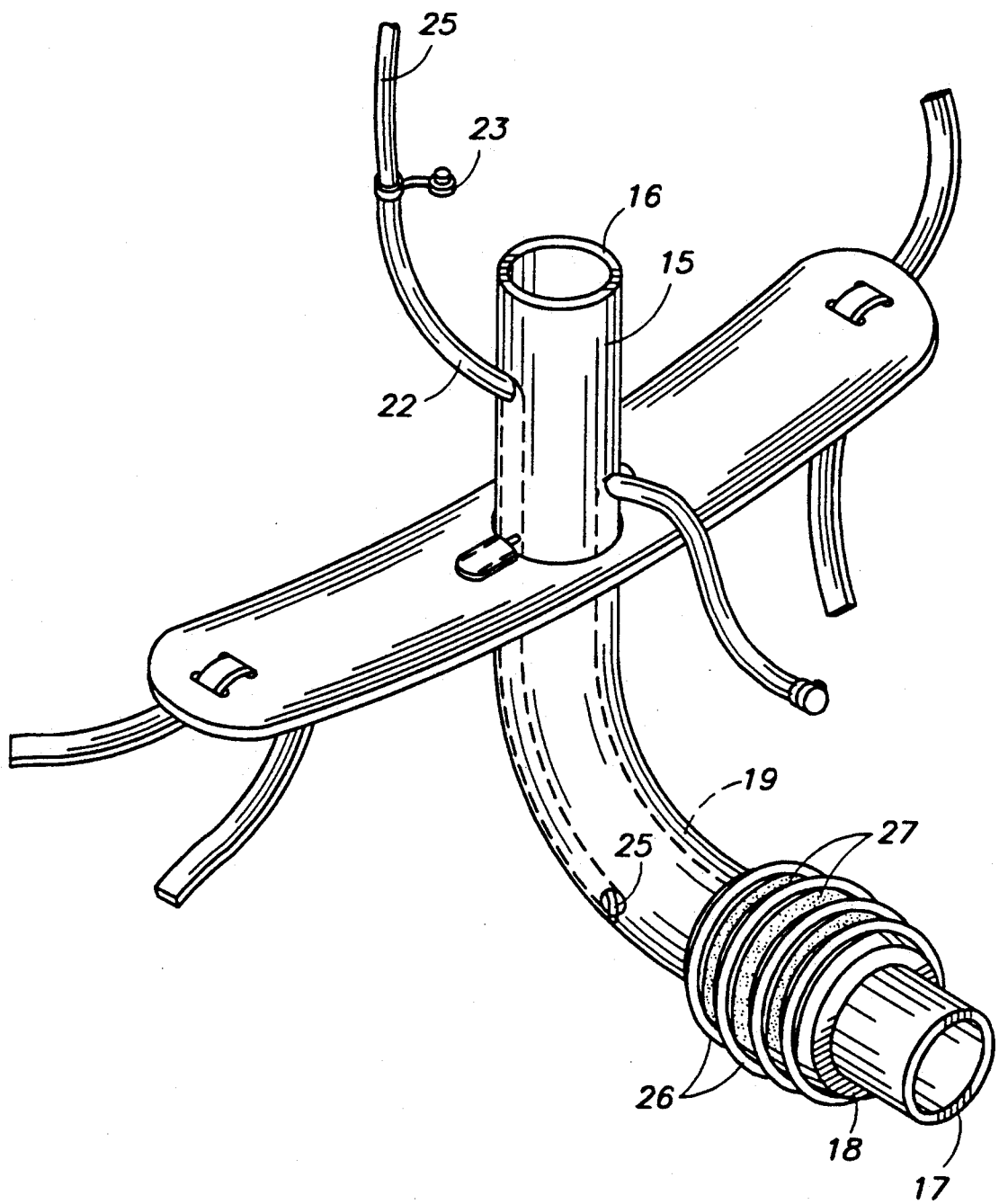
FIG. 3 is an isometric illustration of the invention utilizing a further modified sealing cuff arrangement.

With reference now to the drawings, and in particular to FIGS. 1 to 3 thereof, a new and improved tracheostomy apparatus embodying the principles and concepts of the present invention and generally designated by the reference numeral 10 will be described.

More specifically, the tracheostomy apparatus 10 of the instant invention essentially comprises a flexible support plate member 11, including respective opposed terminal ends, with a respective first and second strap member 12 and 13 directed through the opposed terminal ends of the plate member for securement of the plate member about an individual. The flexible support plate member 11 includes a receiving plate bore 14 pivotally mounting a tracheal tube 15 directed therethrough of a generally "L" shaped configuration formed of a memory retentent flexible material defined by a tube upper end 16 and a tube lower end 17. An expandable balloon seal 18 or cuff is fixedly mounted about the tracheal tube 15 adjacent the lower end 17. An inflation tube 19 in pneumatic communication with the seal 18 is mounted fixedly within the tracheal tube 15 from the seal 18 through the receiving plate bore 14 and is of a flexible construction and separated from the tracheal tube 15 above the receiving bore 14. An inflation tube cap 20 is removably mounted relative to the upper terminal end of the inflation tube 19 to permit inflation of the balloon seal 18.

A directing tube 22 includes a directing tube exit opening 23a directed through the wall of the tracheal tube 15 adjacent to and above the balloon seal 18, with the directing tube 22 positioned interiorly of the tube and extending therealong and projecting through the tracheal tube 15 adjacent the upper terminal end 16 thereof and includes a flexible portion spaced from the tube in its projection from the tracheal tube, with a directing tube cap 23 removably mounted relative to the upper terminal end of the directing tube. The directing tube slidably receives a catheter tube 25 that is slidably directed through the directing tube and directed into the exit opening 23a to remove various debris relative to the tracheal tube 15 above the balloon seal 18.

FIG. 2 illustrates the balloon seal, including a plurality of spaced parallel sealing ribs 26, with the organization as set forth in FIG. 3 including an adhesive paste 27 formed between the sealing ribs 26, wherein the sealing ribs 26 and the adhesive paste 27 of optional use enhance sealing within a windpipe structure of an individual.

Accordingly, the function and operation of the above structure should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A tracheostomy apparatus, comprising,
a flexible support plate member, the flexible support plate member including a first end spaced from a second end, and
a first strap mounted through the first end, with a second strap mounted through the second end for securement of the first and second straps about an individual for mounting the plate member about the individual, and
a receiving plate bore directed medially through the plate member between the first end and the second end, with a tracheal tube including a tracheal tube upper end and a tracheal tube lower end, with the tracheal tube lower end oriented below the plate member and the tracheal tube upper end positioned above the plate member, and
the tracheal tube includes an expandable balloon seal fixedly mounted in surrounding relationship relative to the tracheal tube adjacent the tracheal tube lower end below the plate member, and the balloon seal including an inflation tube in pneumatic communication with the balloon seal, the inflation tube fixedly mounted and secured to an interior surface of the tracheal tube below the plate member, and the inflation tube extending above the plate member and separated from the tracheal tube, and an inflation tube cap removably mounted to the inflation tube at an upper terminal end thereof spaced above the plate member, and
a directing tube fixedly mounted to an interior surface of the tracheal tube, the directing tube including a directing tube exit opening directed through the tracheal tube adjacent an upper terminal end of the balloon seal, and the directing tube projecting exteriorly of the tracheal tube adjacent the tracheal tube upper end, and a directing tube cap mounted to a directing tube upper terminal end spaced above the plate member, and
a catheter tube slidably received through the directing tube extending above the directing tube upper terminal end and extending into the directing tube exit opening, and
a plurality of parallel sealing ribs fixedly mounted to an exterior surface of the balloon seal coextensive therewith, and
an adhesive paste mounted coextensively between adjacent sealing ribs, and
a plurality of diametrically opposed pivot leg supports fixedly mounted to the support plate member, with each pivot leg support directed into the tracheal tube to pivotally mount the tracheal tube relative to the receiving plate bore.

* * * * *